United States Patent [19]
Schumacher et al.

[11] Patent Number: 6,129,728
[45] Date of Patent: Oct. 10, 2000

[54] METHOD AND APPARATUS FOR MANDIBULAR OSTEOSYNTHESIS

[75] Inventors: Brian S. Schumacher; Kevin T. Stone; Jeffrey A. Duncan, all of Jacksonville, Fla.

[73] Assignee: Walter Lorenz Surgical, Inc., Jacksonville, Fla.

[21] Appl. No.: 09/025,140

[22] Filed: Feb. 18, 1998

[51] Int. Cl.⁷ .................................................. A61B 17/56
[52] U.S. Cl. .............................. 606/71; 606/69; 606/73; 606/104
[58] Field of Search ................... 606/69, 70, 71, 606/73

[56] References Cited

U.S. PATENT DOCUMENTS

| | | |
|---|---|---|
| 1,105,105 | 7/1914 | Sherman . |
| 2,489,870 | 11/1949 | Dzus . |
| 2,494,229 | 1/1950 | Collison . |
| 2,631,584 | 3/1953 | Purificato . |
| 3,488,779 | 1/1970 | Christensen . |
| 4,219,015 | 8/1980 | Steinemann . |
| 4,429,690 | 2/1984 | Angelino-Pievani . |
| 4,484,570 | 11/1984 | Sutter et al. ................ 606/72 |
| 4,708,132 | 11/1987 | Silvestrini . |
| 4,903,691 | 2/1990 | Heinl ........................ 606/70 |
| 4,959,065 | 9/1990 | Arnett et al. ................ 606/61 |
| 4,973,332 | 11/1990 | Kummer ..................... 606/65 |
| 5,108,395 | 4/1992 | Laurain ...................... 606/61 |
| 5,108,399 | 4/1992 | Eitenmuller et al. ........ 606/77 |
| 5,129,899 | 7/1992 | Small et al. ................. 606/61 |
| 5,147,363 | 9/1992 | Härle ......................... 606/73 |
| 5,151,103 | 9/1992 | Tepic et al. ................. 606/69 |
| 5,180,382 | 1/1993 | Frigg et al. ................. 606/65 |
| 5,269,784 | 12/1993 | Mast .......................... 606/69 |
| 5,303,718 | 4/1994 | Krajicek .................... 128/897 |
| 5,358,367 | 10/1994 | Yang .......................... 411/397 |
| 5,372,598 | 12/1994 | Luhr et al. ................. 606/69 |
| 5,403,136 | 4/1995 | Mathys ....................... 411/310 |
| 5,413,577 | 5/1995 | Pollock ...................... 606/69 |
| 5,474,551 | 12/1995 | Finn et al. .................. 606/61 |
| 5,505,731 | 4/1996 | Tornier ....................... 606/61 |
| 5,520,690 | 5/1996 | Errico et al. ................ 606/61 |
| 5,569,247 | 10/1996 | Morrison ..................... 606/61 |
| 5,591,167 | 1/1997 | Laurain et al. .............. 606/61 |
| 5,601,553 | 2/1997 | Trebing et al. ............. 606/61 |
| 5,601,554 | 2/1997 | Howland et al. ............ 606/61 |
| 5,607,428 | 3/1997 | Lin ............................ 606/69 |
| 5,653,710 | 8/1997 | Härle ......................... 606/73 |
| 5,676,667 | 10/1997 | Hausman ..................... 606/69 |

Primary Examiner—Michael Buiz
Assistant Examiner—David O. Reip
Attorney, Agent, or Firm—Harness, Dickey & Pierce, P.L.C.

[57] ABSTRACT

A system for mandibular reconstruction generally includes an elongated locking plate having a plurality of internally threaded apertures and a plurality of fasteners. Each fastener includes a main body portion having an upper threaded shaft and a lower threaded shaft. The lower threaded shaft is adapted to engage the mandible. Each fastener further includes a removable head portion internally threaded for engaging the upper shaft portion and externally threaded for engaging a selected one of the internally threaded apertures of the locking plate. In the preferred embodiment, the thread leads of the head portion and lower shaft of the main body portion are identical. A method of mandibular osteosynthesis utilizes the system of osteosynthesis and generally comprises the steps of temporarily securing the elongated locking plate to the mandible with at least one fastener by engaging the threads of the lower portion with the mandible and threadably engaging the head with the locking plate, unthreading the head portion from the main body of the fastener to thereby allow displacement of the locking plate from the mandible without removing the fasteners from the mandible, performing a surgical procedure (e.g., removal of a cancerous growth), and re-securing the elongated plate to the fastener with the removable head portion.

23 Claims, 3 Drawing Sheets

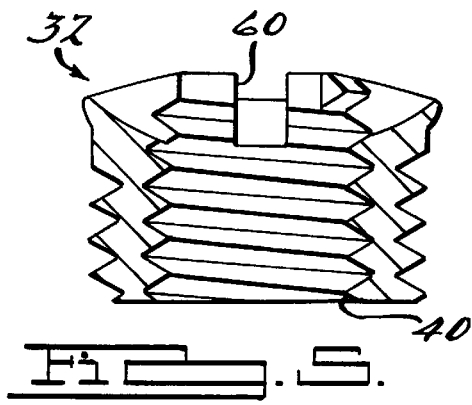
Fig. 5.
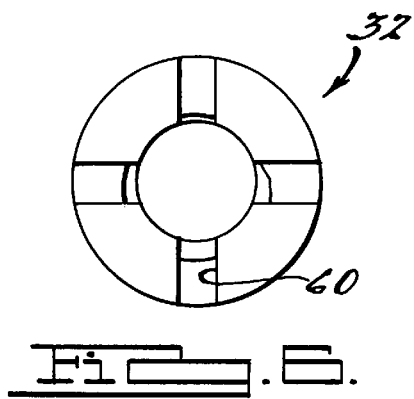
Fig. 6.
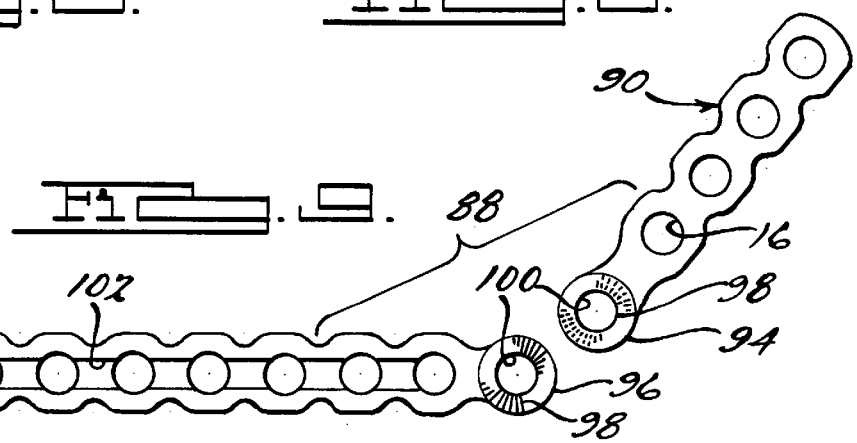
Fig. 9.
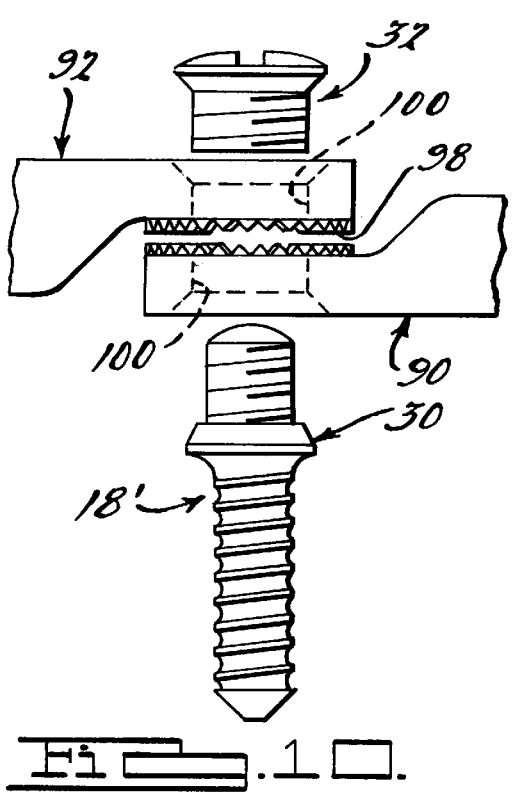
Fig. 10.
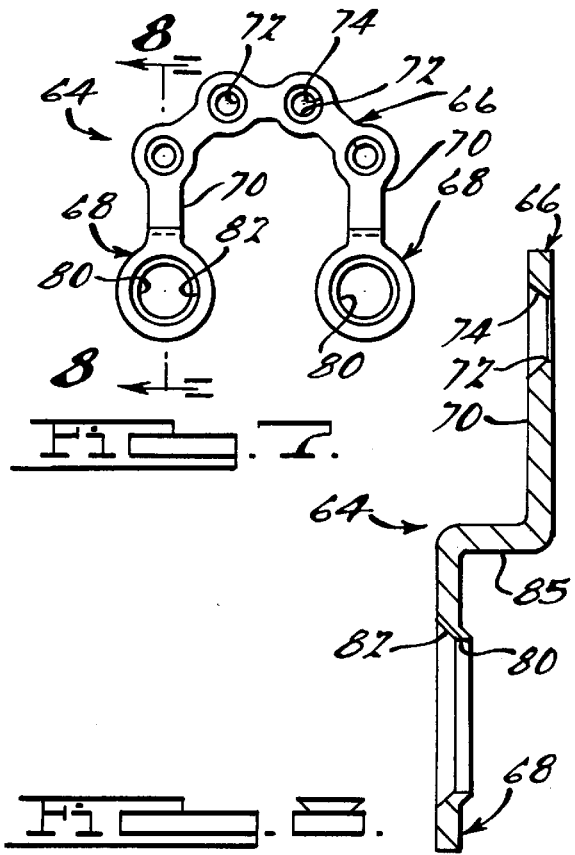
Fig. 7.
Fig. 8.

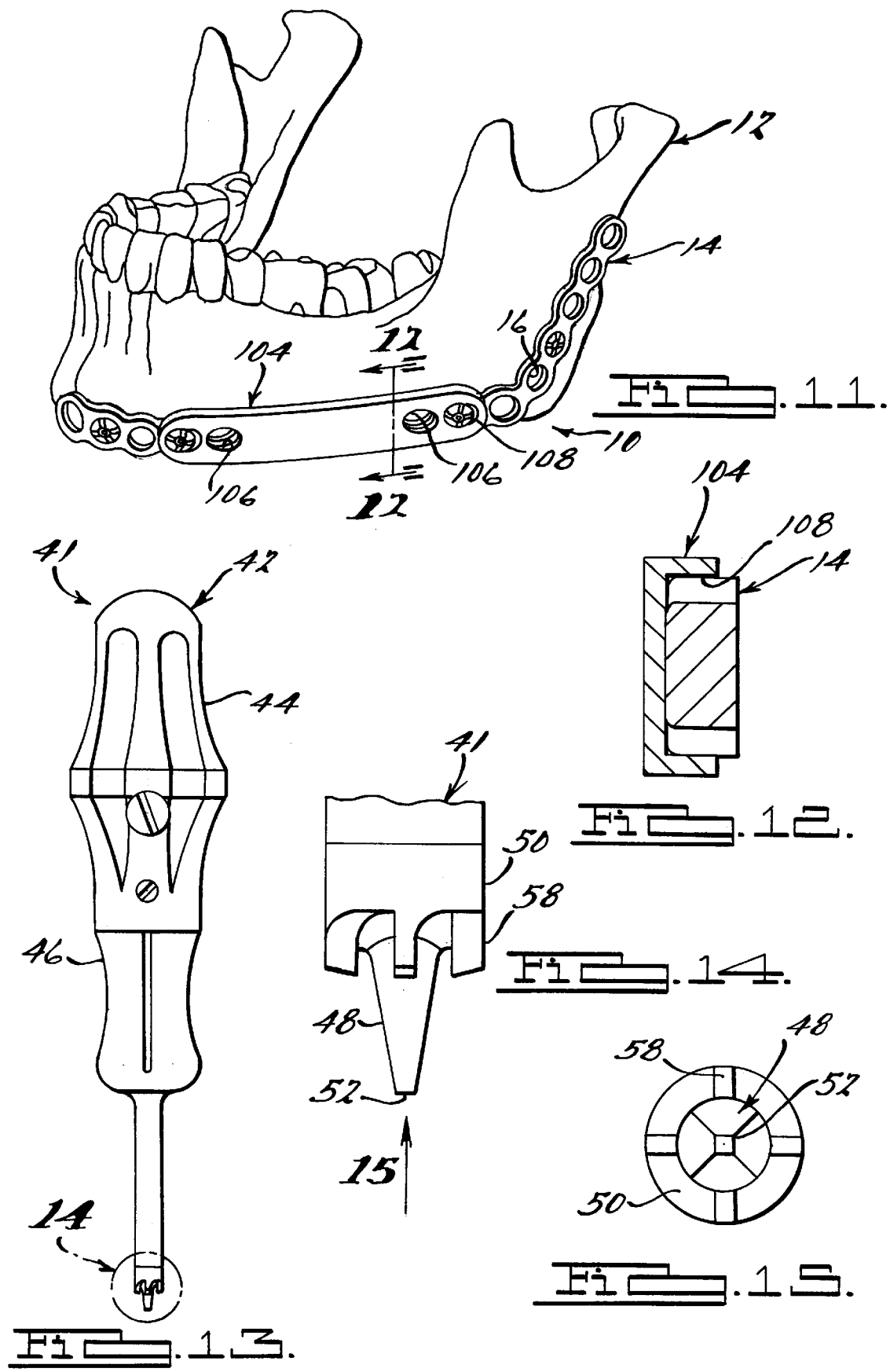

METHOD AND APPARATUS FOR MANDIBULAR OSTEOSYNTHESIS

BACKGROUND OF THE INVENTION

1. Field of the Invention

The present invention relates to surgical applications for the repair of bone fractures and deformities. More particularly, the present invention relates to a method and apparatus for mandibular osteosynthesis.

2. Discussion of the Related Art

In various orthopedic surgical procedures, it is necessary to align and secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed in the desired position during bone regeneration.

It is known in the art to provide metal plates for the repair of bone fractures. These plates are generally secured to bone portions with screws. Among other applications, such plates and fasteners are used to provide rigid stabilization of orthopedic and craniofacial fractures. The plates conventionally employed for cranial and facial osteosynthesis generally comprise small, generally flat, elongated sections of metal. The sections contain round and perhaps elongated screw holes at various points along their lengths for fastening the sections to bone.

Because no surface of the human skeleton is completely flat, existing plates must be extensively twisted, formed and bent during surgery to conform to portions of the skeleton on which they are to be affixed. Significant time is expended during surgery for shaping and re-shaping metal plates adequately to conform to desire bone surfaces. This additional time increases anesthesia requirements and operating room time and also increases the potential for infection.

In one commonly used technique for mandibular reconstruction, a flat plate is drawn against the surface of the mandible with a plurality of fasteners, thereby bending the plate to a desired shape. Subsequently, the fasteners and plate are removed to allow surgical access to the mandible (e.g. for removal of a cancerous growth). Finally, the plate is again fastened to the mandible by engaging the fasteners with existing holes in the mandible.

While known systems utilizing plates and fasteners for cranial and facial osteosynthesis have proven to be acceptable for certain applications, such systems are nevertheless susceptible to improvements that may enhance their performance. In this regard, many known systems require time consuming surgical attachment. Additionally, known systems which necessitate the insertion, removal and subsequent reinsertion of fasteners into the bone negatively affect fastener purchase. Furthermore, many known techniques for cranial facial osteosynthesis disadvantageously position a plate immediately adjacent to the bone which is particularly susceptible to resorption.

SUMMARY OF THE PRESENT INVENTION

In one form, the present invention relates to a method for mandibular osteosynthesis which includes the general step of securing an elongated locking plate to a bone with a plurality of fasteners each including a main body portion having an upper shaft portion and a lower shaft portion. Each fastener further includes a head member removably attached to the upper shaft portion. The method of the present invention further includes the general step of removing the locking plate from the bone by removing the removable head member of each fastener from its main body portion.

In another form, the present invention comprises a system for osteosynthesis of a mandible including an elongated locking plate and at least one fastener. The elongated locking plate has a plurality of internally threaded apertures. Each of the at least one fastener has a main body portion with an externally threaded lower shaft portion and an upper shaft portion. The at least one fastener further has a head member adapted to removably engage the upper shaft portion. The head member is externally threaded for engaging one of the plurality of internally threaded apertures. The externally threaded shaft portion and the externally threaded head member preferably have a common thread lead and an identical thread pitch.

An advantage of the present invention is the provision of a method and apparatus for mandibular osteosynthesis which quickly and easily contours a plate to the mandible without sacrificing fastener purchase with the bone.

A related advantage of the present invention is the provision of a method and apparatus for mandibular osteosynthesis which incorporates a threaded fastener having a removable head.

Another advantage of the present invention is the provision of a method and apparatus for osteosynthesis which incorporates a locking plate with an upwardly curved forward end that more accurately cooperates with the geometry of the human mandible.

Another advantage of the present invention is the provision of a method and apparatus for mandibular osteosynthesis which incorporates an auxiliary reinforcement member adapted to be removably attached to a locking plate.

Another advantage of the present invention is the provision of a method and apparatus for mandible osteosynthesis which incorporates a plate reinforcement member which may be selectively secured to a locking plate for increased strength in areas of significant loss of bone mass.

BRIEF DESCRIPTION OF THE DRAWINGS

FIG. 5 is a cross-sectional view taken along the line 5—5 of FIG. 4.

FIG. 6 illustrates an end view of the head of the fastener shown in FIG. 4 according to the teachings of the preferred embodiment of the present invention.

FIG. 7 is a view of the auxiliary reinforcement member of FIG. 1.

FIG. 8 is an enlarged cross-sectional view taken along the lines 8—8 of FIG. 7.

FIG. 9 is an illustration of a pair of links in accordance with the teachings of the present invention.

FIG. 10 is a fragmentary exploded view of the pair of links of FIG. 9 and a cooperating anchor member.

FIG. 11 is a perspective view similar to FIG. 1, illustrating an alternative locking plate and an alternative auxiliary reinforcement member of the mandibular osteosynthesis system of the present invention operatively associated with a human mandible.

FIG. 12 is a cross-sectional view taken along the line 12—12 of FIG. 11.

FIG. 13 is an illustration of a tool of the mandibular osteosynthesis system of the present invention.

FIG. 14 is an enlarged view illustrating the detail shown in circle 14 identified in FIG. 13.

FIG. 15 is an enlarged end view of the tool taken in the direction of arrow 15 shown in FIG. 14.

DETAILED DESCRIPTION OF THE PRESENT INVENTION

The following description of the preferred embodiment of the present invention is merely exemplary in nature and is in no way intended to limit the invention or its application or uses.

Figure 1:
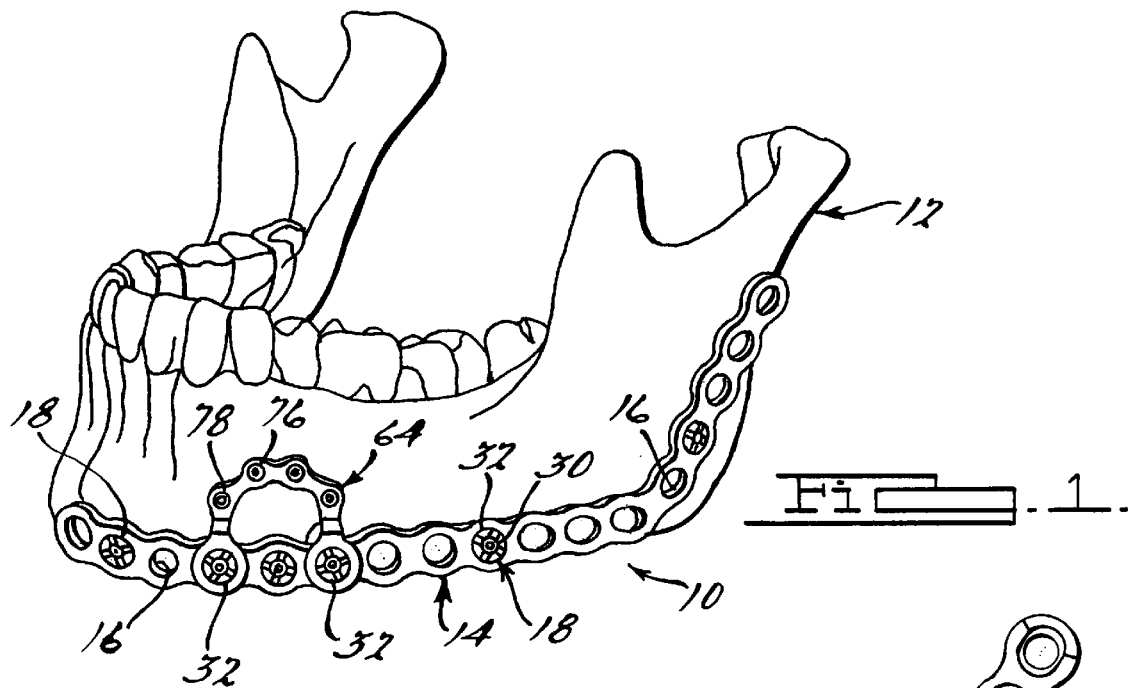
FIG. 1 is a perspective view of a mandibular osteosynthesis system constructed in accordance with the teachings of the preferred embodiment of the present invention illustrated in operative association with a human mandible.

Referring to FIG. 1, a system constructed in accordance with a preferred embodiment of the present invention is generally identified with reference numeral 10. The system 10 is shown operatively associated with a human mandibular 12. However, it will become apparent to those skilled in the art that certain aspects of the present invention have applicability for other surgical applications.

Figure 2:
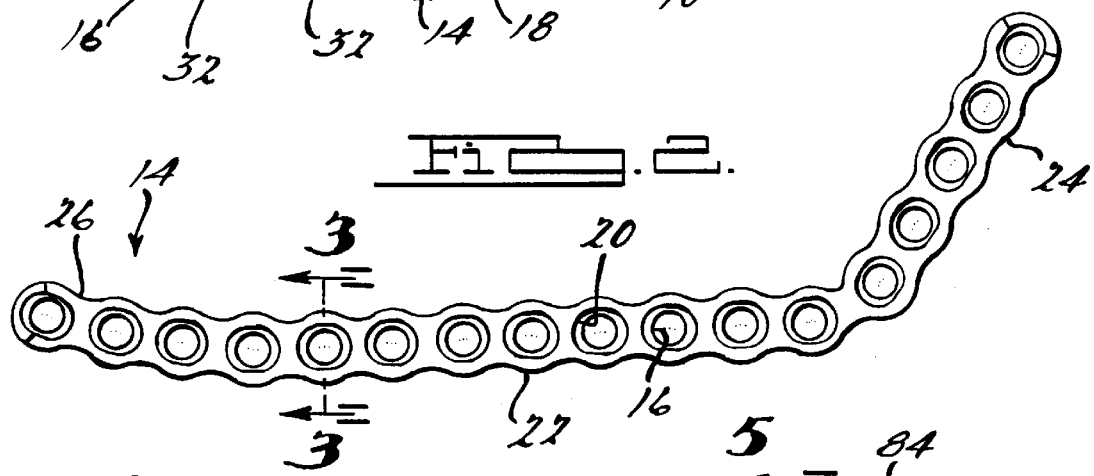
FIG. 2 is an illustration the locking plate shown in FIG. 1 according to the teachings of the preferred embodiment of the present invention.
Figure 3:
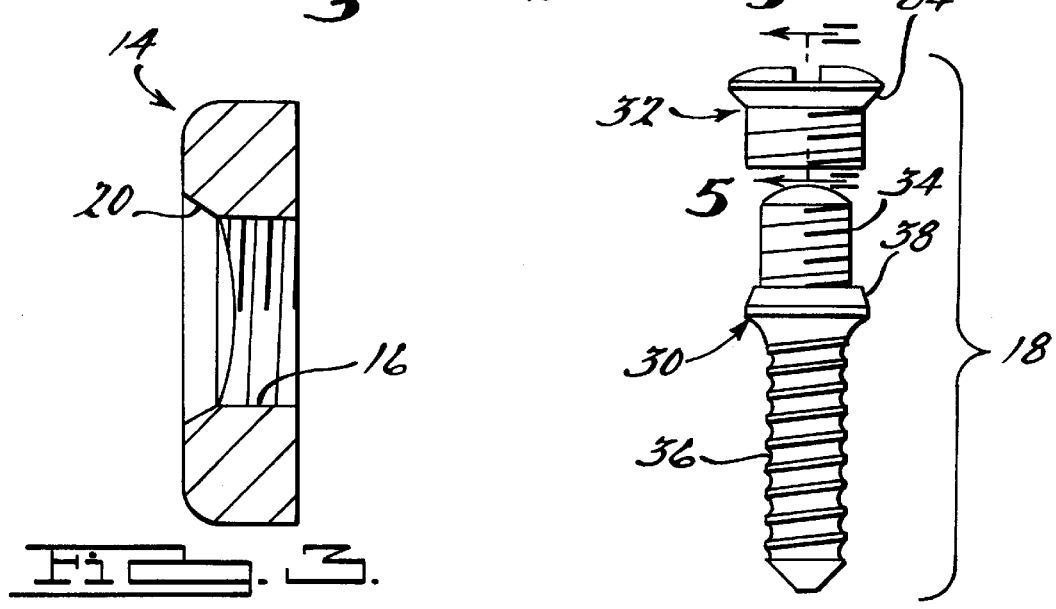
FIG. 3 is a cross-sectional view taken along the line 3—3 of FIG. 2.

With continued reference to FIG. 1 and additional references to FIGS. 2 and 3, the system 10 of the present invention is shown to include an elongated plate 14. The plate 14 is formed to include a plurality of apertures 16, each adapted to receive a fastener 18 for interconnecting the plate 14 with the mandible 12. The apertures preferably include an oval countersink 20 and are internally threaded. For this reason, the plate 14 will be interchangeably referred to herein as a locking plate 14.

The locking plate 14 is shown to generally include a central portion 22, and first and second ends 24 and 26. The first end 24 is precontoured in an anterior-posterior direction to cooperate with the shape of the mandible 12. The second end 24 is also curved upwardly in the plane of the central portion 22, this curvature of the second end 26 cooperates with the contour of the human mandible 12 when the locking plate 14 follows the shape of the mandible 12 in a medial-lateral direction.

In one application, the locking plate 14 is constructed of titanium. More preferably, the locking plate 14 is constructed from commercially pure, grade 2 or grade 4 titanium. However, it will be appreciated by those skilled in the art that other materials having suitable performance characteristics may be employed. Preferably, the locking plate 14 is inelastically deformable so as to retain its shape once contoured to cooperate with the shape of the mandible 12.

Figure 4:
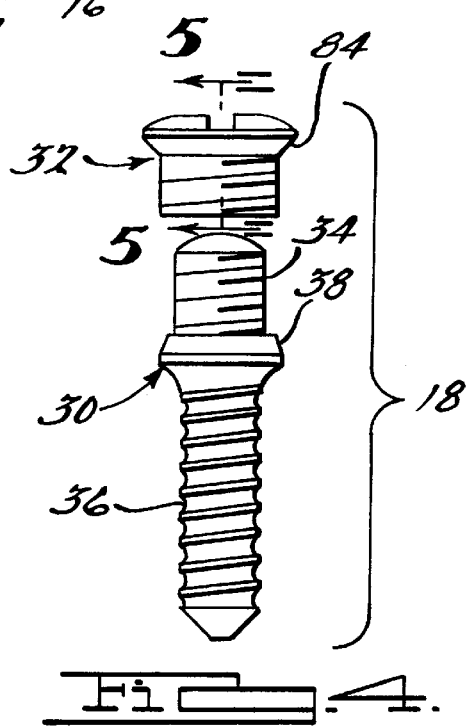
FIG. 4 is an exploded view of one of the fasteners shown in FIG. 1 according to the teachings of the preferred embodiment of the present invention.

With additional reference to FIGS. 4–6, the fastener 18 of the present invention is shown to generally include a main body 30 and a head member 32. The main body 30 includes an upper shaft portion 34 and a lower shaft portion 36. The lower shaft portion 36 is externally threaded and adapted to engage the mandible or bone 12 in a conventional manner. Insertion of the lower shaft portion into the bone is limited by a flange 38 interdisposed between the upper and lower shaft portions 34 and 36. The upper shaft portion 32 is also externally threaded and adapted to engage an internally threaded aperture 40 of the head member 32. The head member 32 is externally threaded for engaging one of the plurality of internally threaded apertures 16 of the locking plate 14.

In one application, the thread pitches of the upper shaft portion 34, lower shaft portion 36 and the thread pitch of the external threads of the head member 32 are common. The external threads of the head member 32 and the externally threaded lower shaft portion 36 have a common thread lead. In the exemplary embodiment illustrated, the externally threaded lower shaft portion 36 has a single lead configuration while the external threads of the upper shaft portion 34 and head member 32 have a double lead configuration.

In use, a malleable template (not shown) is positioned on the mandible 12 and bent to the general shape of the cooperating bone surface. Next, the locking plate 14 is bent to approximately the shape of the template and positioned on the mandible 12 so that certain apertures 16 may be selectively used as a guide for drilling holes (not specifically shown) in the mandible 12 for receiving the fasteners 18. A first of the fasteners 18 is passed through a selected one of the apertures 16 and rotated so that the externally threaded lower portion 36 is driven into the hole in the mandible 12. For example, the first end 24 of the locking plate 14 may be first secured to the mandible 12 with a first fastener 18. As the externally threaded lower portion 36 of the fastener 18 is driven into the bone 12, the external threads of the head member 32 simultaneously engage the internally threaded aperture 16 of the locking plate 14. This is possible as a result of the common thread lead shared between the lower portion 36 and the head member 32.

Additional fasteners 18 are used to interconnect the locking plate 14 with the bone 12 in a substantially identical manner. As shown in FIG. 1, four (4) fasteners are used to interconnect the locking plate 14 with the bone 12. However, it will be appreciated by those skilled in the art that any number of fasteners 18 may be employed depending on a particular application. In one application, the order of the fastener insertion linearly progresses along the locking plate 14 from one end (e.g. the first end 24) to the second end (e.g. the second end 26). As additional fasteners are engaged with the bone 12, the locking plate 14 is drawn into its operative position adjacent to the bone 12.

At this point of the surgical procedure, the head members 32 of each of the threaded fasteners 18 are unthreaded from their respective upper portions 34. This allows the surgeon to displace the locking plate 14 from the fasteners 18 and provides access to the bone 12 for accomplishing a desired surgical procedure (e.g., removal of a cancerous growth). When the locking plate 14 is removed, it retains its shape due to the inelastic deformation. When the surgical procedure is complete, the locking plate 14 is replaced by inserting the upper portions 34 of the fasteners 18 through the selective apertures 14 and simultaneously threading the internal threads of the aperture 16 with the external threads of the upper portion 34 and the external threads of the head member 32 with the internal threads of the aperture 16. Since the fasteners 18 are not removed from the bone 12 after initial insertion, fastener/bone purchase is not compromised.

With reference to FIGS. 13–15, one suitable tool for use in connection with the system 10 of the present invention is shown and generally identified with reference numeral 41. The tool includes a handle 42 having an upper portion 44 and a lower portion 46. The upper and lower portions 44 and 46 are rotatable relative to one another about a longitudinal axis of the tool 41. The upper portion 44 is adapted to rotate with a first drive portion 48, while the lower portion 46 of the handle 42 is adapted to rotate with a second drive portion 50. The first drive portion 48 includes a generally rectangular tip 52 adapted to engage a generally rectangular aperture 54 provided in a top surface 56 of the upper shaft portion 34 of each fastener 18. The second drive portion 50 is illustrated to include four (4) drive elements equally spaced about the first drive member 48. The drive elements 58 are adapted to engage a corresponding number of slots 60 equally spaced about the head member 32 of each fastener 18.

After the holes are drilled into the mandible 12, the surgeon selects a fastener with the head portion 32 threaded onto the upper shaft portion 34 of the main body 30 and engages the drive elements 58 of the tool 41 with the slots 60 of the head member 32 simultaneously. Simultaneously, the tip 52 of the drive member 48 engages the rectangular aperture 54 of the upper shaft portion 34. The surgeon grasps the upper and lower portions 44 and 46 of the handle 42 and rotates the tool 41 in a conventional manner. This action causes the head member 32 to threadably engage an aperture 16 of locking plate 14 and simultaneously causes the threads of the lower shaft portion 36 of the fastener 18 to engage the hole provided in the bone 12.

Once all of the fasteners 18 are initially inserted into the bone 12, the surgeon again engages the head 32 with the drive elements 58. The thumb and forefinger are used to rotate the lower portion 46 of the handle 42 and in turn to rotate the head portion 32 of the fastener 18 in a counter-clockwise direction. Simultaneously, the palm and remaining fingers grasp the upper portion 44 of the handle 42 so that the lower portion 46 can be rotated relative thereto. This action removes the head member 32 from its aperture 16. Since the main body portion 30 of the fastener 18 is not simultaneously rotated, the head portion 32 is simultaneously unthreaded therefrom. In a similar manner, the head portion 32 is returned to threaded engagement with both the aperture 16 of the plate 14 and the upper shaft portion 32 of the main body portion 30 after the desired surgical procedure is performed on the mandible 12.

When the locking plate 14 is operatively associated with the mandible 12 as shown in FIG. 1, the locking plate 14 is adjacent to but slightly displaced from the bone 12. In this regard, the flange 38 which is interdisposed between the upper and lower externally threaded portions 34 and 36 of the fasteners 18 limits downward translation of the removable head member 32. The thickness of the head member 32 is greater than the thickness of the locking plate 14. As a result, when a head members 32 is completely threaded on to the upper portion 34 of an associated fastener 18, the head member 32 extends rearward beyond the locking plate 14 and the locking plate 14 is displaced from the bone 12. Such spacing reduces absorption of the bone which would otherwise be present if the locking plate 14 were to directly contact the bone 12.

With continued reference to FIG. 1 and additional reference to FIGS. 7 and 8, an auxiliary reinforcement member 64 is illustrated. FIG. 1 shows the auxiliary reinforcement member 64 operatively interconnecting a portion of the mandible 12 and the locking plate 14. The auxiliary reinforcement member 64 is intended to reinforce fractured or otherwise weakened portions of the bone 12.

In the exemplary embodiment illustrated, the auxiliary reinforcement member 64 is shown to generally include a bone attachment portion 66 and a pair of plate attachment portions 68. The plate attachment portions 68 are each interconnected to the bone attachment portion 66 through a leg portion 70. In the embodiment illustrated, the bone attachment portion 66 is generally arcuate in shape and includes a plurality of apertures 72. Each of the apertures 72 includes a countersunk portion 74. The apertures 72 are each adapted to receive a threaded fastener 76. The threaded fastener 76 includes a head 78 adapted to seat in the countersunk portion 74 of the aperture 72 and a threaded shaft (not shown) for engaging a portion of the mandible 12. The head 78 of the threaded fastener 76 further includes a generally rectangular aperture substantially identical to the aperture 54 of the threaded fastener 18. As such, the threaded fastener 76 may be inserted and removed with the first drive portion 48 of the tool 41. Alternatively, a separate tool may be used to drive the fastener 76.

The plate engagement portions 68 of the auxiliary is reinforcement member 64 are generally circular in shape and include an aperture 80 having a countersunk portion 82. As shown in FIG. 1, each of the plate engaging portions 68 may be interconnected to the plate 14 with a head portion 32 of the fastener 18. A tapered flange portion 84 (shown in FIG. 4) of the removable head 32 seats in the countersink 74 of the aperture 72 thereby securing the auxiliary reinforcement member 64 to the plate 14 when the external threads of the removable head 32 are engaged with the internal threads of one of the plate apertures 16.

As shown more specifically in FIG. 8, each of the legs 70 are connected to its associated plate engagement portion 68 through an intermediate portion 85. The intermediate portion 85 extends perpendicular to the plane of the bone engagement portion 66 and the plane of the plate engagement portion 68. As a result, the plate engagement portion 66 is stepped down from bone engagement portion 68.

With reference to FIGS. 9 and 10, a link system 88 constructed in accordance with the teachings of the present invention is illustrated. The link system 88 is intended to function as an alternative structure for the locking plate 14 and generally includes first and second links 90 and 92 which are preferably shown to be substantially linear in shape. Each of the links 90 and 92 includes a plurality of apertures 16 substantially identical to the apertures 16 of the locking plate 14. The apertures 16 of the first and second links 90 and 92 are internally threaded and function with one or more fasteners 18 as discussed above. It will be understood by those skilled in the art that either of the first and second links 90 and 92 may have a non-linear shape.

The first and second links 90 and 92 are preferably shown to include cooperating ends 94 and 96, respectively. To provide means for positively locating the first and second links 90 and 92 angularly relative to one another, the cooperating ends 94 and 96 of the first and second links 90 and 92 are each provided with serrations 98 which circumferentially surround an aperture 100. In the embodiment illustrated, the apertures 100 surrounded by the serrations 98 are not internally threaded. The first and second links 90 and 92 are secured to one another and in turn to the bone 12 by a fastener 18'. The fastener 18' is largely identical to the fastener 18 described in connection with FIGS. 4–6. As such, identical reference numerals will be used to identify equivalent elements. The fastener 18' differs from the fastener 18 in that the external diameter of the head 32 is smooth, thereby permitting the first and second link members 90 and 92 to rotate relative to the fastener 18', effectively defining a pivot.

In the embodiment illustrated, the second link 92 of the link system 88 is shown to include a longitudinally extending groove 102. The groove 102 intersects the apertures 16 of the link 92 and functions to increase bending strength of the link 92. It will be understood by those skilled in the art that a similar groove may be added to the first link 90 and also incorporated into the locking plate 14 of FIGS. 1 and 2.

In the preferred embodiment, the fasteners 18 and 18' are constructed from 6AL4V titanium (ti64). However, it will be appreciated by those skilled in the art that other materials of having suitable strength and biocompatible characteristics may be incorporated.

Turning finally to FIGS. 11 and 12, a link reinforcement member 104 of the system 10 of the present invention is illustrated. FIG. 11 illustrates the link reinforcement member 104 operatively interconnected to a locking plate 14 which is substantially identical to that described above with respect to FIGS. 1 and 2. The locking plate 14 is in turn secured to the mandible 12. FIG. 12 is a cross-sectional view illustrating the cooperating relationship between the locking plate reinforcement member 104 and the locking plate 14. The link reinforcement member 104 is intended to reinforce the locking plate 14 at areas where significant bone mass may be absence.

The reinforcement member 104 is illustrated to include a plurality of apertures 106 adapted to align with apertures 16 of the locking plate 14. As shown most clearly in FIG. 12, the locking plate reinforcement member 104 defines a groove 108 adapted to receive the locking plate 14. In use, the plate reinforcement member 104 is placed over the locking plate 14 such that the locking plate 14 is positioned within the groove 108 and the apertures 106 are aligned with the apertures 16. To secure the reinforcement member 104 to the plate 14, a head portion 32 of the fastener 18 is used in a manner substantially identical to the interconnection of the auxiliary reinforcement plate 64 and the locking plate 14. In this regard, the tapered portion 84 of the removal head 32 seats in a countersink portion 108 of the aperture 106 and the removable head 32 threadably engages an aligning aperture 16 of the locking plate 14. If desired, a main body portion 30 of the fastener 18 may also be employed for purposes of providing an additional point of attachment to the mandible 12.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention. For example, the configuration of the locking plate 14 shown in the drawings is one example of a locking plate suitable for use with the teachings of the present invention. It will be understood by those skilled in the art that various other shapes may be employed. For example, the locking plate 14 may be straight, angled, curved or any combination thereof. In certain applications, the locking plate 14 may extend about the entire mandible 12.

What is claimed is:

1. A method of surgically repairing a bone with an elongated locking plate having a plurality of apertures, the method comprising the steps of:
   providing a fastener having a main body including an upper shaft portion and a lower shaft portion, said fastener further including a head member removably attached to said upper shaft portion;
   securing said elongated locking plate adjacent to the bone with said fastener by threadably engaging said head member with said locking plate;
   removing said head member of said fastener from said main body portion; and
   removing said elongated locking plate from adjacent said bone.

2. The method of surgically repairing a bone of claim 1, wherein the step of securing said elongated locking plate adjacent to the bone with said fastener includes the step of engaging the bone with the fastener.

3. The method of surgically repairing a bone of claim 1, wherein the step of removing said elongated locking plate from adjacent said bone comprises the step of maintaining engagement between the bone and said fastener.

4. The method of surgically repairing a bone of claim 1, wherein said step of securing said elongated locking plate adjacent to the bone with said fastener simultaneously includes the steps of threadably engaging the bone with said lower shaft portion of said fastener and threadably engaging the locking plate with said head member of said fastener.

5. The method of surgically repairing a bone of claim 1, further including the step of inelastically deforming the elongated locking plate to conform with a portion of the bone.

6. The method of surgically repairing a bone of claim 1, wherein the step of removing said head member of said fastener from said main body portion simultaneously includes the step of unthreading said head member from said locking plate.

7. The method of surgically repairing a bone of claim 1, wherein the step of securing the elongated locking plate adjacent to the bone with said fastener includes the step of maintaining a space between the elongated plate and the bone.

8. The method of surgically repairing a bone of claim 1, wherein the bone is a mandible.

9. A system for osteosynthesis of a mandible, the system comprising:
   an elongated locking plate having a plurality of internally threaded apertures; and
   at least one fastener having a main body portion with an externally threaded lower shaft portion and an upper shaft portion, said at least one fastener further having a head member adapted to removably engage said upper shaft portion, said head member being externally threaded for engaging one of said plurality of internally threaded apertures;
   wherein said head member is internally threaded and said upper shaft portion is externally threaded.

10. The system for osteosynthesis of a mandible of claim 9, wherein said upper shaft portion has a thread lead substantially identical to said externally threaded shaft portion and said externally threaded head member.

11. The system for osteosynthesis of a mandible of claim 9, wherein each fastener of said at least one fastener includes a flange portion interbetween said lower shaft portion and said upper shaft portion, said flange portion adapted to maintain a space between said elongated locking plate and the mandible.

12. The system for osteosynthesis of a mandible of claim 9, further comprising to tool for independently rotating said head member and said main body portion of said fastener, said tool includes a handle having first and second portions rotatable relative to one another, said first portion connected for rotation to a first drive member adapted to engage said head member, said second portion connected for rotation to a second drive member adapted to engage said main body portion.

13. A method of surgically repairing a bone with an elongated locking plate having a plurality of apertures, the method comprising the steps of:

providing a fastener having a main body including an upper shaft portion and a lower shaft portion, said fastener further including a head member removably attached to said upper shaft portion;

securing said elongated locking plate adjacent to the bone with said fastener;

removing said head member of said fastener from said main body portion;

removing said elongated locking plate from adjacent said bone;

wherein the step of securing the elongated locking plate adjacent to the bone with said fastener includes the step of maintaining a space between the elongated plate and the bone.

14. A method of osteosynthesis of a mandible, the method comprising the steps of:

providing an elongated locking plate having a plurality of apertures;

providing a plurality of fasteners for securing said elongated locking plate adjacent to the mandible, each of said fasteners including a main body portion having a lower shaft portion and an upper shaft portion, each of said fasteners further including a head member removably attached to said upper shaft portion;

threadably engaging the mandible with said lower shaft portion of each of said fasteners;

engaging said head member of each of said fasteners with said locking plate so as to position said elongated locking plate adjacent to the mandible;

removing said head member of each said fastener from said upper shaft portion;

displacing said elongated locking plate from adjacent the mandible to thereby expose the mandible for surgical access;

securing said elongated locking plate to said fastener by reattaching each head member to an associated upper shaft portion; and maintaining a space between the elongated locking plate and the bone.

15. A system for osteosynthesis of a mandible, the system comprising:

an elongated locking plate having a plurality of internally threaded apertures; and at least one fastener having a main body portion with an externally threaded lower shaft portion and an upper shaft portion, said at least one fastener further having a head member adapted to removably engage said upper shaft portion, said head member being externally threaded for engaging one of said plurality of internally threaded apertures;

wherein each fastener of said at least one fastener includes a flange portion interbetween said lower shaft portion and said upper shaft portion, said flange portion adapted to maintain a space between said elongated locking plate and the mandible.

16. A system for osteosynthesis of a mandible, the system comprising:

an elongated locking plate having a plurality of internally threaded apertures;

at least one fastener having a main body portion with an externally threaded lower shaft portion and an upper shaft portion, said at least one fastener further having a head member adapted to removably engage said upper shaft portion, said head member being externally threaded for engaging one of said plurality of internally threaded apertures; and a tool for independently rotating said head member and said main body portion of said fastener, said tool includes a handle having first and second portions rotatable relative to one another, said first portion connected for rotation to a first drive member adapted to engage said head member, said second portion connected for rotation to a second drive member adapted to engage said main body portion.

17. A method of surgically repairing a bone with an elongated locking plate having a plurality of apertures, the method comprising the steps of:

providing a fastener having a main body including an upper shaft portion and a lower shaft portion, said fastener further including a head member removably attached to said upper shaft portion;

securing said elongated locking plate adjacent to the bone with said fastener by engaging said head member with said locking plate;

maintaining a space between the elongated plate and the bone;

removing said head member of said fastener from said main body portion; and removing said elongated locking plate from adjacent said bone.

18. The method of surgically repairing a bone of claim 17, wherein the step of securing said elongated locking plate adjacent to the bone with said fastener includes the step of engaging the bone with the fastener.

19. The method of surgically repairing a bone of claim 17, wherein the step of removing said elongated locking plate from adjacent said bone comprises the step of maintaining engagement between the bone and said fastener.

20. The method of surgically repairing a bone of claim 17, wherein said step of securing said elongated locking plate adjacent to the bone with said fastener simultaneously includes the steps of threadably engaging the bone with said lower shaft portion of said fastener and threadably engaging the locking plate with said head member of said fastener.

21. The method of surgically repairing a bone of claim 17, further including the step of inelastically deforming the elongated locking plate to conform with a portion of the bone.

22. The method of surgically repairing a bone of claim 17, wherein the step of securing the elongated locking plate adjacent to the bone with said fastener includes the step of maintaining a space between the elongated plate and the bone.

23. The method of surgically repairing a bone of claim 17, wherein the bone is a mandible.

* * * * *